US006682726B2

(12) United States Patent
Marchesi et al.

(10) Patent No.: US 6,682,726 B2
(45) Date of Patent: Jan. 27, 2004

(54) SELF-FOAMING SHAVING LOTION

(75) Inventors: Jenifer T. Marchesi, Hopkinton, MA (US); Yun Xu, Andover, MA (US); Kenneth T. Dodd, Upton, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/845,853

(22) Filed: Apr. 30, 2001

(65) Prior Publication Data

US 2003/0026775 A1 Feb. 6, 2003

(51) Int. Cl.$^7$ ................................................. A61K 7/06
(52) U.S. Cl. ............................ 424/73; 424/43; 424/47; 424/70.13; 424/70.19; 424/70.11
(58) Field of Search ................. 424/73, 70.13, 424/70.19, 70.11, 43, 47

(56) References Cited

U.S. PATENT DOCUMENTS

| | | | |
|---|---|---|---|
| 3,919,092 A | 11/1975 | Norton et al. | 252/8.55 D |
| 4,145,411 A | 3/1979 | Mende | 424/45 |
| 4,781,847 A | 11/1988 | Weitz | 252/49.3 |
| 4,871,530 A | 10/1989 | Grollier et al. | 424/47 |
| 4,999,183 A | 3/1991 | Mackles et al. | 424/47 |
| 5,104,643 A | 4/1992 | Grollier et al. | 424/47 |
| 5,186,857 A | 2/1993 | Ramirez et al. | 326/377 |
| 5,248,495 A | 9/1993 | Patterson et al. | 424/73 |
| 5,294,438 A | 3/1994 | Chang et al. | 424/73 |
| 5,326,556 A | 7/1994 | Barnet et al. | 424/73 |
| 5,342,617 A | 8/1994 | Gold | 424/405 |
| 5,451,396 A | 9/1995 | Villars | 424/73 |
| 5,500,211 A | 3/1996 | George et al. | 424/73 |
| 5,560,859 A | 10/1996 | Hartmann et al. | 510/135 |
| 5,635,171 A | 6/1997 | Nadaud | 424/78.03 |
| 5,756,081 A | 5/1998 | Wdowik | 424/73 |
| 5,858,343 A | 1/1999 | Szymczak | 424/73 |
| 5,914,103 A | 6/1999 | Armbruster et al. | 424/73 |
| 5,976,520 A | 11/1999 | Babinski et al. | 424/73 |
| 6,440,912 B2 | 8/2002 | McGee et al. | 510/140 |

FOREIGN PATENT DOCUMENTS

| | | |
|---|---|---|
| EP | 0 586 295 | 3/1993 |
| FR | 2 555 443 | 3/1985 |
| GB | 2 047 736 A | 3/1980 |
| WO | WO 91/07943 | 6/1991 |
| WO | WO 94/02109 | 2/1994 |
| WO | WO 00/39273 | 7/2000 |

OTHER PUBLICATIONS

*Harry's Cosmeticology*, Seventh Edition, J.B. Wilkinson and R.J. Moore (editors), Chemical Publishing, New York, 1982, pp. 156–189.

Primary Examiner—Jyothsna Venkat
(74) Attorney, Agent, or Firm—Stephan P. Williams

(57) ABSTRACT

The present invention is directed to a self-foaming shaving composition in the form of a lotion. The shaving composition comprises water, a water dispersible surface active agent capable of forming a lather, a volatile self-foaming agent, and a water soluble thickening agent wherein the composition is in the form of a self-foaming lotion having an elastic modulus (G') of about 100 to about 1000 Pascals, preferably about 200 to about 900 Pa, most preferably about 400 to about 800 Pa (measured with a rheometer at frequency 1 Hz, oscillatory stress range 0.01–1.0 Pa, temperature 5° C., Gap 1000 $\mu$m). The present invention is also directed to an improved shaving method in which a shaving composition of the present invention is applied to an area of skin, then said area is shaved, preferably with a wet razor.

16 Claims, No Drawings

SELF-FOAMING SHAVING LOTION

BACKGROUND OF THE INVENTION

This invention relates to self-foaming shaving compositions in the form of a lotion.

An extensive discussion regarding the formulation of various shaving preparations may be found in *Harry's Cosmeticology*, Seventh Edition, J. B. Wilkinson and R. J. Moore (editors), Chemical Publishing, New York, 1982, pp. 156–189. Currently, the most widely used forms of shaving preparation are the types referred to as instant foams and self-foaming gels (also known as post-foaming gels). Instant foams comprise water, a dispersed or solubilized surface-active agent (e.g., a soap, an anionic, cationic, amphoteric, or nonionic surface-active agent, or a combination of these agents), and a propellant/blowing agent. They may also include ingredients such as foam builders, foam stabilizers, emollients, viscosity modifiers, lubricants, humectants, preservatives, and fragrance. They are dispensed from pressurized aerosol containers in the form of a rich foam lather for spreading by hand on the area to be shaved. Self-foaming gels include many of the same ingredients as instant foams. These are oil-in-water emulsions that are formulated as thick, stiff gels which have incorporated into the composition a small amount of blowing agent (typically a volatile hydrocarbon). When the gel is rubbed onto a warm surface, like skin, the blowing agent volatilizes and causes the gel to turn into a foam lather. Typically, self-foaming gels have an elastic modulus (G') greater than 1500 Pascals ("Pa") when measured using a rheometer (e.g., AR-1000-N, TA Instruments, 4 cm acrylic plate) at frequency 1 Hz, oscillatory stress range 0.01–1.0 Pa, temperature 5° C., gap 1000 $\mu$m.

SUMMARY OF THE INVENTION

The present invention is directed to a self-foaming shaving composition in the form of a lotion. The shaving composition comprises water, a water dispersible surface active agent capable of forming a lather, a volatile self-foaming agent, and a water soluble thickening agent, wherein the composition is in the form of a self-foaming lotion having an elastic modulus (G') of about 100 to about 1000 Pascals, preferably about 200 to about 900 Pa, most preferably about 200 to about 800 Pa (measured with a rheometer (e.g., AR-1000-N, TA Instruments, 4 cm acrylic plate) at frequency 1 Hz, oscillatory stress range 0.01–1.0 Pa, temperature 5° C., Gap 1000 $\mu$m). The present invention is also directed to an improved shaving method in which a shaving composition of the present invention is applied to an area of skin, then said area is shaved, preferably with a wet razor.

DETAILED DESCRIPTION OF THE INVENTION

The shaving composition of the present invention is in the form of a self-foaming lotion. Such a formulation will typically comprise, by weight, about 60% to about 93%, preferably about 70% to about 85%, water, about 2% to about 25%, preferably about 5% to about 20%, water dispersible (or soluble) surface active agent capable of forming a lather, about 1% to about 6%, preferably about 2% to about 4%, volatile self-foaming agent, and about 0.01% to about 5%, preferably about 0.05% to about 2%, more preferably about 0.1% to about 1%, most preferably about 0.2% to about 0.8%, water soluble thickening agent.

The water dispersible surface active agent capable of forming a lather may comprise a soap, a detergent, an anionic surfactant, a non-ionic surfactant, or a mixture of one or more of these. The soaps include, for example, the sodium, potassium and lower alkanolamine (preferably triethanolamine) salts of $C_{10}$ to $C_{20}$, preferably $C_{12}$ to $C_{18}$, fatty acids. Typical fatty acids include lauric, oleic, coconut oil, myristic, palmitic and stearic acid and mixtures thereof. The preferred fatty acids are palmitic and stearic. For purposes of the present invention, the soaps are also intended to include the interrupted soaps such as the sodium, potassium and lower alkanolamine (preferably triethanolamine) salts of N-fatty acyl sarcosines wherein the fatty acyl moiety has 10 to 20, preferably 12 to 18, carbon atoms. Typical sarcosines include stearoyl sarcosine, myristoyl sarcosine, palmitoyl sarcosine, oleoyl sarcosine, lauroyl sarcosine, cocoyl sarcosine and mixtures thereof. The soaps (including the interrupted soaps) may be utilized in preneutralized form (i.e. as the sodium, potassium or alkanolamine salt) or in the free acid form followed by subsequent neutralization with sodium hydroxide, potassium hydroxide and/or alkanolamine (preferably triethanolamine). In any event, the final composition must contain sufficient base to neutralize or partially neutralize the soap component and adjust the pH to the desired level. It is most preferred that the compositions of the present invention include a conventional soap (i.e., a salt of a fatty acid, as opposed to an interrupted soap).

The water dispersible surface active agent may also optionally include a non-ionic, amphoteric and/or anionic surfactant. Suitable non-ionic surfactants will typically have an HLB of 14 or more and include the polyoxyethylene ethers of fatty alcohols, acids and amides, particularly those having 10 to 20, preferably 12 to 18, carbon atoms in the fatty moiety and about 8 to 60, preferably 10 to 30, ethylene oxide units. These include, for example, PEG-150 Distearate, Oleth-20, Steareth-21, Ceteth-20, and Laureth-23. Other non-ionic surfactants include the polyoxyethylene ethers of alkyl substituted phenols, such as Nonoxynol-4 and Nonoxynol-20, fatty alkanolamides such as Lauramide DEA and Cocamide MEA, polyethoxylated sorbitan esters of fatty acids, such as Polysorbate-20, lauryl polyglucoside, sucrose laurate, and polyglycerol 8-oleate. Suitable amphoteric surfactants include, for example, the betaines and sultaines such as cocoamidopropyl betaine, coco dimethyl carboxymethyl betaine, coco sultaine and the like. Suitable anionic surfactants include, for example, the sodium, potassium, ammonium and substituted ammonium salts (such as the mono-, di- and triethanolamine salts) of $C_8$–$C_{22}$, preferably $C_{12}$–$C_{18}$, alkyl sulfates (e.g. sodium lauryl sulfate, ammonium lauryl sulfate), alkyl sulfonates (e.g. ammonium lauryl sulfonate), alkylbenzene sulfonates (e.g. ammonium xylene sulfonate), acyl isethionates (e.g. sodium cocoyl isethionate), acyl lactylates (e.g. sodium cocoyl lactylate) and alkyl ether sulfates (e.g. ammonium laureth sulfate). While the surface active agent may include up to about 8% of non-ionic, amphoteric and/or anionic surfactants, it is generally preferred that the shaving composition include less than 2%, preferably less than 1%, of these surfactants.

The self-foaming agent may be any volatile hydrocarbon or halohydrocarbon with a sufficiently low boiling point that it will volatilize and foam the lotion upon application to the skin, but not so low that it causes the lotion to foam prematurely. The typical boiling point of such an agent generally falls within the range of −20° to 40° C. Preferred self-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio (IP:IB) of about 1:1 to about 9:1, preferably about 2:1 to about 7:1, more preferably about 3:1 to about 6:1. The self-foaming agent will normally be selected so as to provide a vapor pressure at 20° C. of about 5 to about 20 psig, preferably about 5 to about 15 psig. The self-foaming agent will be present in an amount to provide the shaving composition with a sufficiently rapid turnover—that is, transition from lotion to foam when contacted with the skin—typically, in about 2 to about 40 seconds, preferably in about 5 to about 30 seconds.

The shaving compositions of the present invention also include a water soluble thickening agent suitable for thickening the composition to a lotion form having the desired viscosity and/or elastic modulus. Typically, the lotion will have a viscosity in the range of about 5 to about 250 Pa-s, preferably about 10 to about 100 Pa-s at shear rate of 0.01/s (measured with a rheometer (e.g.

AR-1000-N, TA Instruments, 4 cm acrylic plate) at frequency 1 Hz, oscillatory stress range 0.01–800 Pa, temperature 5° C., Gap 1000 $\mu$m). However, viscosity is not an ideal property to define shaving lotions. The preferred rheological property by which the lotions of the present invention may be defined is elastic modulus. The self-foaming lotions will typically have an elastic modulus (G') of about 100 to about 1000 Pa, preferably about 200 to about 900 Pa, most preferably about 200 to about 800 Pa (measured with a rheometer (e.g. AR-1000-N, TA Instruments, 4 cm acrylic plate) at frequency 1 Hz, oscillatory stress range 0.01–1.0 Pa, temperature 5° C., Gap 1000 $\mu$m).

Suitable water soluble thickening agents for inclusion in the self-foaming shaving lotions of the present invention include alkyl glycols, polyalkyl glycol ethers, polyacrylic acids, polyacrylamides, modified cellulose polymers, gums, resins and starches. Typical thickening agents include, for example, hydroxyalkyl cellulose polymers such as hydroxyethyl cellulose and hydroxypropyl cellulose (sold under the trademarks "Natrosol" and "Klucel" respectively), copolymers of acrylic acid and polyallyl sucrose (sold under the trademark "Carbopol"), polyvinylpyrrolidone, polyvinylacohol, carboxymethyl cellulose, and cellulose methyl ether (sold under the trademark "Methocel"). The preferred thickening agents include the high molecular weight polyethylene oxides (MW is one million or more) and natural or synthetic polysaccharide gums, particularly when used in combination. The combination of polyethylene oxide and natural or synthetic polysaccharide gum is especially preferred because it has been found that these polymers interact synergistically to provide the desired elastic modulus while reducing friction between the razor cartridge and the skin.

The polyethylene oxides which may be used effectively in compositions of the present invention include one or more polyethylene oxides of molecular weight of about one million or higher, typically up to about five million. Such polyethylene oxides include, for example, one or more of the following: PEG-23M (WSR N-12K (Union Carbide; M.Wt.≅1,000,000), PEG-45M (WSR N-60K (Union Carbide; M.Wt.≅2,000,000), PEG-90M (WSR-301 (Union Carbide; M.Wt.≅4,000,000), PEG-115M (Polyox Coagulant (Union Carbide; M.Wt.≅5,000,000). A preferred polyethylene oxide will have a molecular weight between about two million and about four million, most preferably about two million. If desired, some lower molecular weight polyethylene oxides may be blended with the aforementioned polyethylene oxides of molecular weight one million or higher, although this is not preferred.

The natural or synthetic gums which may be used effectively in compositions of the present invention include one or more polysaccharide gums. These gums usually consist of a hetero- or homo-polysaccharide backbone with varying degrees and types of substitution including, but not limited to, methylation, ethoxylation, propoxylation, sulfonation, or addition of further sugar residues singly or in groups. Substitution may be naturally occurring or synthetically performed or a combination of these. Suitable gums include, but are not limited to, xanthan gum, carrageenan gum, guar gum, locust bean gum, and hydroxypropyl guar gum. Carrageenan gum is preferred.

An especially preferred embodiment of the present invention is a self-foaming lotion which contains a minimum of ingredients. This provides the benefits of simple formulation and reduced costs. A simple formulation consists essentially of water, surface active agent capable of forming a lather, self-foaming agent and the thickening agent. The thickening agent preferably includes polyethylene oxide (MW of one million or higher) and natural or synthetic gum (e.g. carrageenan, xanthan, etc.). The term "consist(ing) essentially of" is not intended to exclude materials that do not affect the basic and fundamental characteristics of the composition. For example, one might normally include in a simple formula a fragrance, a colorant, a preservative (e.g., antimicrobial or antioxidant), or even a small amount (e.g. 2% or less) of an agent to improve application aesthetics, but none of these are viewed as an ingredient that materially affects the basic and fundamental characteristics of the composition. Preferably the total amount of all such non-essential ingredients will be less than 5%, more preferably less than about 2%, of the composition by weight.

Although not necessary to forming a useful shaving composition, other cosmetic ingredients may be added to improve the application aesthetics and/or achieve other shave benefits. For example, the composition may include one or more of the following components: beard wetting agents, skin conditioning agents (e.g. vitamins A, C and E, aloe, allantoin, panthenol, alpha-hydroxy acids, phospholipids, triglycerides, botanical oils, amino acids), cleansing agents, lathering agents, emollients, humectants (e.g., glycerin, sorbitol, propylene glycol), fragrances, colorants, antioxidants, preservatives, etc.

The shaving composition may optionally include about 0.1% to 10%, preferably about 0.1 to 2%, of one or more oily materials selected from a non-volatile paraffinic hydrocarbon fluid (e.g., mineral oil, hydrogenated polyisobutene), a non-volatile silicone (e.g., dimethicone, phenyl trimethicone), a fatty alcohol (e.g., myristyl alcohol, stearyl alcohol, octyl dodecanol), or a fatty ester (e.g., isopropyl myristate).

The shaving compositions of the present invention may be packaged in any suitable dispenser normally used for dispensing shaving gels. These include collapsible tubes, pump or squeeze containers, and aerosol-type dispensers with a barrier to separate the shaving composition from the propellant required for expulsion. The latter type of dispensers include: (1) mechanically pressurized bag-in-sleeve systems in which a thin-walled inner bag containing the product is surrounded by an outer elastic sleeve that is expanded during the product filling process and provides dispensing power to expel the product (e.g., the ATMOS System available commercially from the Exxel Container Co.); (2) manually activated air pump spray devices in which a pump system is integrated into the container to allow the user to pressurize the container with air in order to expel the product (e.g., the "AIRSPRAY" system available from Airspray International); (3) piston barrier systems in which the product is separated from the driving means by a tight-fitting piston which seals to the side of the container and may be driven by a spring under tension, by a vacuum on the product side of the piston, by finger pressure, by gas pressure to the piston, or by a variety of other means known to the packaging industry; and (4) bag-in-can (SEPRO) systems in which the product is contained in a flexible bag within a can, with a suitable propellant injected into the space between the can and the flexible bag. It is preferred to protect the composition from oxidation and heavy metal contamination. This can be achieved, for example, by purging the composition and container with nitrogen to remove oxygen and by utilizing inert containers (e.g. plastic bottles or bags, aluminum cans or polymer coated or lined cans).

The shaving compositions of the present invention have many unique characteristics. They are neither foams nor gels, nor are they a non-aerosol form (such as is typically packaged in a squeeze tube). They are self-foaming lotions which provide a rich, cushioning, high-volume lather, a rapid turnover (i.e. transition to foam lather), good adherence to skin, excellent lubricity, and good coverage.

The invention may be further described by the following examples in which all parts and percentages are by weight.

Examples 1–5

Self-Foaming Shave Lotion

| Ingredient | Weight Percent | | | | |
|---|---|---|---|---|---|
| | Ex. 1 | Ex. 2 | Ex. 3 | Ex. 4 | Ex. 5 |
| Palmitic acid | 8.17 | 8.17 | 8.17 | 8.99 | 8.17 |
| Triethanolamine (99%) | 5.00 | 5.00 | 5.00 | 5.50 | 5.00 |
| Sorbitol (70%) | 4.33 | 4.33 | 4.33 | 2.89 | 3.85 |
| Isopentane/isobutane (4:1) | 3.85 | 3.85 | 3.85 | 3.85 | 3.85 |
| Carrageenan[1] | 0.48 | 0.48 | 0.48 | 0.53 | 0.43 |
| PEG-45M[2] | 0.12 | 0.12 | 0.12 | 0.24 | 0.12 |
| Phospholipid[3] | 0.48 | 0.48 | 0.48 | | 1.92 |
| PEG-150 Distearate | 0.24 | 0.24 | 0.24 | 0.15 | 0.16 |
| Beeswax[4] | 0.19 | 0.19 | 0.19 | | |
| Fragrance/dye | 0.19 | 0.15 | 0.19 | 0.19 | 0.19 |
| Vitamins/Botanicals/Amino Acids | 0.18 | 0.13 | 0.21 | 0.12 | 0.19 |
| Polypropylene glycol | | | | | 0.02 |
| Water | 76.76 | 76.87 | 76.70 | 77.55 | 76.10 |

[1]Genuvisco TPH-1 (Hercules-Aqualon Corp.)
[2]WSR N-60K (Union Carbide; M. Wt. ≅ 2,000,000)
[3]Phosal 50 SA (phospholipid, safflower oil, ethanol; American Lecithin Co.)
[4]Beeswax SP-422P (Strahl & Pitsch Inc.)

| Ingredient | Weight Percent | | | |
|---|---|---|---|---|
| | Ex. 6 | Ex. 7 | Ex. 8 | Ex. 9 |
| Palmitic acid | 8.54 | | | 6.57 |
| Stearic acid | | | | 0.98 |
| Triethanolamine (99%) | 5.23 | 0.72 | 3.95 | 4.18 |
| Glycerin | 2.11 | | 2.11 | |
| Sod. Olefin $C_{14-16}$ Sulfonate[1] | | 2.40 | | |
| Stearoyl/Myristoyl Sarcosine[2] | | | 10.78 | |
| Isopentane/isobutane (4:1) | 3.85 | 3.85 | 3.85 | 2.00 |
| Carrageenan[3] | 0.53 | | 0.53 | 0.98 |
| Carbopol EDT 2020 | | 0.48 | | |
| PEG-45M[4] | 0.21 | | 0.21 | 0.11 |
| PEG-23M[5] | | 0.16 | | |
| Polyquaternium-22[6] | | 0.48 | | |
| Laurylamidopropyl Betaine[7] | | | | 6.80 |
| Polyquaternium-39[8] | | | | 4.90 |
| Oleth-20 | | | | 1.47 |
| Lauramide DEA | | | | 0.98 |
| Water | 79.53 | 91.91 | 78.57 | 71.03 |

[1]BioTerge AS 40 (Stephan Chemical Co.)
[2]Hamposyl SM Sarcosine (Hampshire Chemical Inc.)
[3]Genuvisco TPH-1 (Hercules-Aqualon Corp.)
[4]WSR N-60K (Union Carbide; M. Wt. ≅ 2,000,000)
[5]WSR N-12K (Union Carbide; M. Wt. ≅ 1,000,000)
[6]Merquat 280 (Calgon Corp.)
[7]Amphosal LB (36%, Stephan Chemical Co.)
[8]Merquat 3330 (Calgon Corp.)

The above-described compositions were made in the following manner: The water soluble components (i.e., polymers (gum, polyethylene oxide, Carbopol), glycerin, sorbitol) are added to water and mixed until the polymers are completely dissolved (about 30 min.). The mixture is then heated and the palmitic acid (or pre-melted sarcosine or sulfonate) is added at about 60° C. and well mixed while the heating continues. At 80°–85° C. the triethanolamine is added and mixed for about 40 minutes. While cooling the soap phase, the phospholipids, beeswax and PEG-150 distearate (and vitamin E if used) are separately mixed at about 65° C. until melted, then added to the soap phase and mixed for about 30 minutes. While cooling this mixture to 30° C., the remaining ingredients are added at about 45° C. and mixed well. The concentrate (at about 20° C.) is then mixed with the volatile self-foaming agent (at about 5° C.) in a pressurized vessel, then filled into bottom-gassed cans.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A shaving composition comprising water, a water dispersible surface active agent capable of forming a lather, a volatile self-foaming agent, and a water soluble thickening agent, wherein the composition is in the form of a self-foaming lotion having an elastic modulus (G') of 200 to about 1000 PA measured with a rheometer at frequency 1 Hz, oscillatory stress range 0.01–1.0 Pa, temperature 5° C. Gap 1000 $\mu$m.

2. The shaving composition of claim 1 comprising, by weight, about 60% to about 93% water, about 2% to about 25% water dispersible surface active agent capable of forming a lather, about 1% to about 6% volatile self-foaming agent, and about 0.01% to about 5% water soluble thickening agent.

3. The shaving composition of claim 1 comprising, by weight, about 70% to about 85% water, about 5% to about 20% water dispersible surface active agent capable of forming a lather, about 2% to about 4% volatile self-foaming agent, and about 0.05% to about 2% water soluble thickening agent.

4. The shaving composition of claim 2 having an elastic modulus (G') of about 200 to about 900 Pa.

5. The shaving composition of claim 3 having an elastic modulus (G') of about 400 to about 800 Pa.

6. The shaving composition of claim 2 wherein the water soluble thickening agent comprises polyethylene oxide having a molecular weight of one million or more.

7. The shaving composition of claim 2 wherein the water soluble thickening agent comprises a natural or synthetic polysaccharide gum.

8. The shaving composition of claim 2 wherein the water soluble thickening agent comprises a natural or synthetic polysaccharide gum and polyethylene oxide having a molecular weight of one million or more.

9. The shaving composition of claim 8 wherein the water dispersible surface active agent comprises a soap.

10. The shaving composition of claim 9 wherein the polysaccharide gum is selected from the group consisting of xanthan gum, carrageenan gum, guar gum, locust bean gum and hydroxypropyl guar gum.

11. The shaving composition of claim 2 wherein the volatile self-foaming agent provides a vapor pressure at 20° C. of about 5 to about 20 psig.

12. The shaving composition of claim 2 wherein the volatile self-foaming agent comprises a mixture of isopentane and isobutane in a weight ratio of about 2:1 to about 7:1.

13. The shaving composition of claim 1 wherein the composition, on contact with human skin, transitions from lotion to foam in about 2 to about 40 seconds.

14. A method of shaving comprising applying to an area of skin a shaving composition and shaving said area of skin, wherein said shaving composition comprises water, a water dispersible surface active agent capable of forming a lather, a volatile self-foaming agent, and a water soluble thickening agent, wherein the composition is in the form of a self-foaming lotion having an elastic modulus (G') of about 200 to about 1000 Pa measured with a rheometer at frequency 1 Hz, oscillatory stress range 0.01–1.0 Pa, temperature 5° C., Gap 1000 $\mu$m.

15. The method of claim 14 wherein said shaving composition is a shaving composition according to any one of claims 2 to 13.

16. The shaving composition of claim 3 having an elastic modulus (G') of about 400 to about 1000 Pa.

* * * * *

UNITED STATES PATENT AND TRADEMARK OFFICE
CERTIFICATE OF CORRECTION

PATENT NO. : 6,682,726 B2
DATED : January 27, 2004
INVENTOR(S) : Jenifer T. Marchesi, Yun Xu and Kenneth T. Dodd It is certified that error appears in the above-identified patent and that said Letters Patent is hereby corrected as shown below:

Column 5,
Lines 52-53, insert -- Examples 6-8, Self-Foaming Shave Lotion --

Column 6,
Line 48, insert -- about -- before "200"
Line 49, change "PA" to -- Pa --
Line 50, change "5° C." to -- 5° C., --

Signed and Sealed this

Twenty-fifth Day of May, 2004

JON W. DUDAS
*Acting Director of the United States Patent and Trademark Office*